United States Patent [19]

Rook et al.

[11] Patent Number: 4,724,144

[45] Date of Patent: Feb. 9, 1988

[54] IMMUNO-THERAPEUTIC COMPOSITION OF KILLED CELLS FROM MYCOBACTERIUM VACCAE

[75] Inventors: Graham A. W. Rook, London; John L. Stanford, Marden, both of England

[73] Assignee: University College London, London, England

[21] Appl. No.: 791,143

[22] PCT Filed: Feb. 15, 1985

[86] PCT No.: PCT/GB85/00064

§ 371 Date: Oct. 16, 1985

§ 102(e) Date: Oct. 16, 1985

[87] PCT Pub. No.: WO85/03639

PCT Pub. Date: Aug. 29, 1985

[30] Foreign Application Priority Data

Feb. 17, 1984 [GB] United Kingdom ............... 8404280

[51] Int. Cl.$^4$ ............................................. A61K 39/04
[52] U.S. Cl. ........................................ 424/88; 424/92; 424/93; 435/68; 435/863; 435/822
[58] Field of Search ............... 424/88, 92, 93; 435/68, 435/863, 822

[56] References Cited

U.S. PATENT DOCUMENTS 3,849,551 11/1974 D'Antonia ........................... 424/88

FOREIGN PATENT DOCUMENTS 0035429 9/1981 European Pat. Off. ............. 424/92
2602177 7/1976 Fed. Rep. of Germany ........ 424/92
2719547 11/1977 Fed. Rep. of Germany ........ 424/92
2466247 4/1981 France .................................. 424/92
1426042 2/1976 United Kingdom .................. 424/92

OTHER PUBLICATIONS

Navalker et al, *Abst. Int. J. Lepr. Other Myabart Dis.*, 1980, 48(4), pp. 388–396.
Baker et al, *Abst. Immunol.*, 1981, 44(3), pp. 593–598.
Leprosy Review 47, pp. 87–91, 1976.
F. M. Collins et al., "Immune Response to Persistent Mycobacterial Infection in Mice", Infection and Immunity, vol. 20, No. 2, May 1978, pp. 430–438.
S. R. Watson et al., "Delayed Hypersensitivity Responses in Mice and Guinea Pigs to Mycobacterium Lebrae, Mycobacterium Vaccae and Mycobacterium Nonchromogeni cum Cytoplasmic Proteins", Biological Abstracts, vol. 69, No. 1, 1980, p. 306, abstract 2847, Infect. Immun. 25(1), 229, 236, 1979.
F. M. Collins et al., "Fernandez and Mitsuda Reactivity in Guinea Pigs Sensitized with Heat–Killed Mycobacterium Leprae: Persistence and Specificity of Skin Reactivity to Soluble and Particulate Antigens", Biological Abstracts, vol. 78, No. 3, 1984, p. 2213, abstract 19506, Int. J. Lepr. 51(4): 481–489, 1983.

*Primary Examiner*—John Kight
*Assistant Examiner*—Garnette D. Draper
*Attorney, Agent, or Firm*—Wegner & Bretschneider

[57] ABSTRACT

"Immuno-therapeutic agents of killed cells prepared from *Mycobacterium Vaccae* that are useful in the treatment of mycobacterial disease, especially tuberculosis or leprosy, in particular as an adjuvant to chemotherapy".

11 Claims, No Drawings

IMMUNO-THERAPEUTIC COMPOSITION OF KILLED CELLS FROM MYCOBACTERIUM VACCAE

This invention relates to immunotherapeutic agents useful in the immunotherapy of mycobacterial disease, especially tuberculosis and leprosy.

The eradication of mycobacterial diseases such as tuberculosis and leprosy by effective treatment is still a primary objective particularly in disease endemic areas such as third world countries of Asia, Africa and South East Asia. Modern drug treatment of these diseases consists of chemotherapy with, for example, rifampicin and isoniazid in the case of tuberculosis and clofazimine and sulphones in the case of leprosy.

Chemotherapy, though effective in killing rapidly metabolising bacilli, is very slow to eliminate "persisters", and this necessitates continuation of treatment for 9 months to a year in the case of tuberculosis, and 5 years or more in the case of leprosy. 'Persisters' are metabolically inactive microorganisms which can survive long exposure to a drug, only becoming susceptible when they start to multiply.

We have now found that the mycobacterium, $M.$ $vaccae$, is especially effective for the immunotherapy of mycobacterial disease, especially tuberculosis and leprosy. Experiments have shown that suspensions containing killed $M.$ $vaccae$ in excess of $10^8$ microorganisms per ml of diluent can be effective in eliminating "persisters" within a short period of time, usually 1 or 2 months. In addition, vaccines based on $M.$ $vaccae$ are easy to manufacture at low cost since $M.$ $vaccae$ can be cultivated in simple media, unlike some other species of mycobacteria, for example $M.$ $leprae$, which can only be cultivated in armadillo tissues which are expensive and not easily obtainable.

The present invention therefore provides an immunotherapeutic agent comprising antigenic material derived from *Mycobacterium vaccae*. The antigenic material is conveniently, and therefore preferably, dead cells of $M.$ $vaccae$, e.g. cells which have been killed by irradiation. The immunotherapeutic agent normally comprises more than $10^8$ microorganisms per ml of diluent, and preferably from $10^8$ to $10^{11}$ killed $M.$ $vaccae$ microorganisms per ml of diluent. The invention includes within its scope antigenic material from $M.$ $vaccae$ for use in therapy in the treatment of mycobacterial disease, e.g. tuberculosis or leprosy, preferably as an adjunct to chemotherapy.

The diluent may be pyrogen-free saline for injection alone, or a borate buffer of pH 8.0. The diluent should be sterile. A suitable borate Buffer is:

$Na_2B_4O_7.10H_2O$: 3.63 g
$H_3BO_3$: 5.25 g
NaCl: 6.19 g
Tween: 0.0005%
Distilled Water: to 1 liter The preferred strain of $M.$ $vaccae$ is one denoted R877R isolated from mud samples from the Lango district of Central Uganda (J. L. Stanford and R. C. Paul, Ann. Soc. belge Med, trop. 1973, 53, 141–389). The strain is a stable rough variant and belongs to the *aurum* sub-species. It can be identified as belonging to $M.$ $vaccae$ by biochemical and antigenic criteria (R. Bonicke, S. E. Jahasz., Zentr albl. Bakteriol. Parasitenkd. Infection skr. Hyg. Abt. 1, Orig., 1964, 192, 133). $M.$ $vaccae$ is believed to be closely similar antigenically to $M.$ $leprae$ (J. L. Stanford et al, British Journal of Experimental Pathology, 1975, 56, 579).

The strain denoted R877R has been deposited at the National Collection of Type Cultures (NCTC) Central Public Health Laboratory, Colindale Avenue, London NW9 5HT, United Kingdom on Feb. 13th, 1984 under the number NCTC 11659.

For the preparation of the immunotherapeutic agent, the microorganism $M.$ $vaccae$ may be grown on a suitable solid medium. A modified Sauton's liquid medium is preferred (S. V. Boyden and E. Sorkin., J. Immunol, 1955, 75, 15) solidified with agar. Preferably the solid medium contains 1.3% agar. The medium inoculated with the microorganisms is incubated to enable growth of the microorganisms to take place, generally at 32° C. for 10 days. The organisms are harvested, then weighed and suspended in a diluent. The diluent may be saline but it preferably also contains a surfactant such as Tween 80. 1 part Tween 80 is preferably used in 300 parts saline. The suspension is diluted with the saline/Tween 80 diluent to give 100 mg of microorganism/ml. For further dilution, borate buffered saline is preferably used to that the suspension contains 10 mg of microorganisms/ml of diluent. The suspension may then be dispensed into 5 ml multidose vials. The microorganisms in the vials are killed using irradiation e.g. from $^{60}$Cobalt at a dose of 2.5 megarads, or by any other means, for example by heat.

The immunotherapeutic agent is in general administered by injection in a volume in the range 0.1–0.2 ml given intradermally. A single dosage may contain from $10^7$ to $10^{10}$ killed $M.$ $vaccae$ microorganisms. It is preferred to administer to patients suffering from mycobacterial disease a single dose containing $10^7$ to $10^{10}$ killed $M.$ $vaccae$. However, the dose may be repeated depending on the condition of the patient.

The immunotherapeutic agent is preferably administered as an adjunct to chemotherapy, and normally 1 to 3 months after starting effective chemotherapy, e.g. with one of the chemotherapeutic agents mentioned above. Thus its effect is designed to be maximal after the majority of bacilli in the lesions, i.e. the metabolically active bacilli, have been killed and the load of bacterial antigenic material has begun to decline.

The invention therefore includes within its scope a method of treating mycobacterial disease, e.g. tuberculosis or leprosy, which comprises administering to a subject suffering therefrom antigenic material derived from *Mycobacterium vaccae* in an amount sufficient to provoke an immune response effective against metabolically inactive cells of mycobacteria.

The immunotherapeutic agent is believed to have two modes of action. It presents the "protective" common mycobacterial antigens to advantage and contains immune suppressor determinants active in regulating disadvantageous immune mechanisms (P. M. Nye et al, Leprosy Review, 1983, 54, 9). As a result of its action, "persister" bacilli are recognised by the immune system by their content of common mycobacterial antigens and effective immune mechanisms are directed against them, in the absence of the tissue necrotic form of immunity usually present in mycobacterial disease (G. A. W. Rook & J. L. Stanford, Parasite Immunology, 1971, 1, 111). Thus "persisters" are eradicated by the action of the body defence mechanism and the period of chemotherapy required is drastically shortened. This dramatically reduces treatment costs, and the problem of patient non-compliance with chemotherapy.

It may be advantageous and is within the scope of the invention to use more than one strain of *M. vaccae*, and/or to include in the immunotherapeutic agent other mycobacterial antigens.

The immunotherapeutic agent may also contain BCG (Bacillus Calmette-Guerin) vaccine, in particular the freeze-dried form of the vaccine, to promote its effect.

The immunotherapeutic agent can contain further ingredients such as adjuvants, preservatives, stabilisers etc. It may be supplied in sterile injectable liquid form or in sterile freeze-dried form which is reconstituted prior to use.

The following Example illustrates the invention.

EXAMPLE

*M. vaccae* is grown on a solid medium comprising modified Sauton's medium solidified with 1.3% agar. The medium is inoculated with the microorganism and incubated for 10 days at 32° C. to enable growth of the microorganism to take place. The microorganisms are then harvested and weighed and suspended in diluent (1 part Tween 80 in 300 parts saline) to give 100 mg of microorganisms/ml of diluent. The suspension is then further diluted with saline to give a suspension containing 10 mg of microorganisms/ml of diluent and dispensed into 5 ml multidose vials. The vials containing the live microorganism are then subjected to radiation from $^{60}$Cobalt at a dose of 2.5 megarads to kill the microorganisms and give the immunotherapeutic agent of the invention, which may (if desired) be further diluted for use.

This immunotherapeutic agent may be administered by intradermal injection in the manner already described.

What is claimed is:

1. An immunotherapeutic agent consisting essentially of killed cells of *Mycobacterium vaccae*.

2. An immunotherapeutic agent according to claim 1 comprising cells of *M. vaccae* which have been killed by irradiation.

3. An immunotherapeutic agent according to claim 1 in sterile injectable liquid form or in sterile freeze-dried form.

4. An immunotherpeutic agent according to claim 1 derived from *M. vaccae* NCTC 11659.

5. An immunotherapeutic agent according to claim 1 in the form of a single dosage unit containing $10^7$ to $10^{10}$ killed cells of *M. vaccae*.

6. An immunotherapeutic agent according to claim 1 which also comprises BCG vaccine.

7. An immunotherapeutic agent according claim 5 which also comprises BCG vaccine.

8. An immunotherapeutic agent according to claim 1 which also comprises one or more additional ingredients selected from adjuvants, preservatives, and stabilizers.

9. Method of treating mycobacterial disease which comprises administering to a subject suffering therefrom, in association with chemotherapy, killed cells of *Mycobacterium vaccae* in an amount sufficient to provoke an immune response effective against mycobacteria that survive the chemotherapy.

10. Method according to claim 9 in which the mycobacterial disease is tuberculosis or leprosy and the mycobacteria are *Mycobacterium tuberculosis* or *M. leprae* respectively.

11. Method according to claim 9 in which the antigenic material comprises cells of *M. vaccae* NCTC11659 which have been killed by irradiation.